(12) United States Patent
Robertson et al.

(10) Patent No.: US 9,677,128 B2
(45) Date of Patent: Jun. 13, 2017

(54) METHODS AND KITS FOR DETECTION OF 5-HYDROXYMETHYLCYTOSINE

(75) Inventors: Adam Brian Robertson, Oslo (NO); John Arne Dahl, Oslo (NO); Arne Klungland, Oslo (NO)

(73) Assignee: OSLO UNIVERSITETSSYKEHUS HF, Oslo (NO)

( * ) Notice: Subject to any disclaimer, the term of this patent is extended or adjusted under 35 U.S.C. 154(b) by 518 days.

(21) Appl. No.: 13/878,909

(22) PCT Filed: Oct. 20, 2011

(86) PCT No.: PCT/US2011/057107
§ 371 (c)(1),
(2), (4) Date: Jul. 11, 2013

(87) PCT Pub. No.: WO2012/054730
PCT Pub. Date: Apr. 26, 2012

(65) Prior Publication Data
US 2013/0323728 A1 Dec. 5, 2013

Related U.S. Application Data

(60) Provisional application No. 61/405,706, filed on Oct. 22, 2010.

(51) Int. Cl.
| | |
|---|---|
| C07H 21/02 | (2006.01) |
| C07K 16/00 | (2006.01) |
| C07K 14/00 | (2006.01) |
| C12Q 1/68 | (2006.01) |

(52) U.S. Cl.
CPC ......... C12Q 1/6827 (2013.01); C12Q 1/6806 (2013.01); *Y10T 436/147777* (2015.01)

(58) Field of Classification Search
None
See application file for complete search history.

(56) References Cited

U.S. PATENT DOCUMENTS

2005/0227235 A1* 10/2005 Carr .................. C12Q 1/6848
435/6.16

FOREIGN PATENT DOCUMENTS

WO 2010/037001 4/2010

OTHER PUBLICATIONS

Dipaolo et al. Molecular Cell. 2005. 17:441-451.*
Grover et al. Angew. Chem. Int. Ed. 2007. 46: 4839-2843.*
Unligil et al. Current Opinion in Structural Biology. 2000. 10: 510-517.*
Levine et al. PNAS. 1960. 46(8): 1038-1043.*
Sabatini et al. The Journal of Biological Chemistry. 2002. 277(31):28150-28156.*
Cross et al. The Embo Journal. 1999. 18(21): 6573-6581.*
Panyutin et al. Acta Oncologica. 1996. 35(7): 817-823.*
Yu et al. Nucleic Acids Res. 2007. 35(7):2107-2115.*
Safarik et al. BioMagnetic Research and Technology. 2004. 2:7.*

(Continued)

*Primary Examiner* — Joseph G Dauner
(74) *Attorney, Agent, or Firm* — Casimir Jones S.C.

(57) ABSTRACT

The present invention relates to methods and kits for the detection of 5-hydroxymethylcytosme (5hmC). In some embodiments, the present invention relates to methods and kits for detection of 5hmC in nucleic acid (e.g., DNA, RNA). In some embodiments, the present invention relates to detection of 5hmC in genomic DNA, e.g., mammalian genomic DNA.

5 Claims, 7 Drawing Sheets

(56) References Cited

OTHER PUBLICATIONS

Flusberg, B. et al., "Direct detection of DNA methylation during single-molecule, real-time sequencing", Nature Methods, vol. 7, No. 6, Jun. 2010: 461-465.

Hendrich, B. et al., "Identification and Characterization of a Family of Mammalian Methyl-CpG Binding Proteins", Molecular and Cellular Biology, Nov. 1998, p. 6538-6547.

Illingworth, R. et al., "CpG islands-'A rough guide'", FEBS Letters 583 (2009) 1713-1720.

Ito, S. et al., "Role of Tet proteins in 5mC to 5hmC conversion, ES cell self-renewal, and ICM specification", Nature Aug. 26, 2010; 466(7310):1129-1133.

Jin, S. et al., "Examination of the specificity of DNA methylation profiling techniques towards 5-methylcytosine and 5-hydroxymethylcytosine", Nucleic Acids Research, 2010, vol. 38, No. 11, e125.

Kriaucionis, S. et al., "The nuclear DNA base, 5-hydroxymethylcytosine is present in brain and enriched in Purkinje neurons", Science May 15, 2009; 324 (5929): 929-930.

Munzel, M. et al., "Quantification of the Sixth DNA Base Hydroxymethylcytosine in the Brain", Angew. Chem. Int. Ed. 2010, 49, 5375-5377.

Nestor, C. et al., "Enzymatic approaches and bisulfite sequencing cannot distinguish between 5-methylcytosine and 5-hydroxymethylcytosine in DNA", BioTechniques 48: 317-319 (Apr. 2010).

Szwagierczak, A. et al., "Sensitive enzymatic quantification of 5-hydroxymethylcytosine in genomic DNA", Nucleic Acids Research 2010, vol. 38, No. 19, e181.

Tahiliani, M. et al., "Conversion of 5-Methylcytosine to 5-Hydroxymethylcytosine in Mammalian DNA by MLL Partner TET1", Science May 15, 2009 vol. 324:930-935.

Tomaschewski, J. et al., "T4-induced alpha- and beta-glucosyltransferase: cloning of the genes and a comparison of their products based on sequencing data", Nucleic Acids Research vol. 13 No. 21 (1985) 7551-7568.

Robertson, A. et. al., "A novel method for the efficient and selective identification of 5-hydroxymethylcytosine in genomic DNA", Nucleic Acids Research, 2011, vol. 39, No. 8, e55.

\* cited by examiner

Figure 6

**JBP1 (*Crithidia fasciculate*) Recombinant (SEQ ID NO:1)**

MGSSHHHHHH SSGLVPRGSH MEPKSKKVKQ DIFNFPDGKD VPTTKEKAEA
YVDALKAHPF YDNVHSVVDV YDSATLRDGK GRVIGVMLRK ALPEHATTAA
GLLSAAAVR TSLRSSMFGG ESPLSGIAGY FDYRGSPVEL KARKTAFTYE
HEKKWPAVFP LVDYVSEIYK SVMPEHWAAQ DSAIPDIVRI HGTPFSTLTI
NSRFRTASHT DAGDFDGGYS CIACIDGDFK GLALGFDDFH VNVPMQPRDV
LVFDSHYFHS NSELEISCPT EEWRRLTCVF YYRSALGEPS SYAEYRRRLA
AAQQDSTAQP VVSSVVEKPN GKNLYKPSTV FPIDPTPFAV VAQLHRLHHC
AAKGLCVHEL LAVPSSPLAV LLFGERLSCS DGIPLRAAEQ KLKANADGAS
RGVTSSGGFS ESDAVLTTAV EKSKYLERDH LSQCISAELL AMWVEARKHW
LRLVATEWAR MIATAPERTD FLWKNKSPMN TAFFDLCEVA KQVMLGLLDK
ETATPTEERH FWSVYAAHLH RACAERLMMP EEAMSLRKLN VKLKDFSFGG
TRYFKDMPVE EQERRVARKA SIEEARRRST AAKDGEQRSN WLTNDAFDYQ
TEDCEVDYAG HGWAVPKQHA KTVTANVHQE AVAATTEAVR VLVVLPRPPS
GDRGDAAVDL PKEVTTSAEW VRLMSSPAVR RVLAAKQRNL TLLPNCNVEA
VSLNFAYHDS LPQKATFDFV VLQHVLSAMP EDAIATDYVS RMRSICTGCL
FVVETDVQCR QYFTLHYPLR VQYDAVAPAF FQLLHRCSYG TPLARTRTKA
EVEALFPFVC CARYKLQGSP MNTVVHLLAL E

Figure 7

β-glucosyltransferase (*T4*) *bgt* Recombinant (SEQ ID NO:2)

MGSSHHHHHH SSGLVPRGSH MKIAIINMGN NVINFKTVPS SETIYLFKVI
SEMGLNVDII SLKNGVYTKS FDEVDVNDYD RLIVVNSSIN FFGGKPNLAI
LSAQKFMAKY KSKIYYLFTD IRLPFSQSWP NVKNRPWAYL YTEEELLIKS
PIKVISQGIN LDIAKAAHKK VDNVIEFEYF PIEQYKIHMN DFQLSKPTKK
TLDVIYGGSF RSGQRESKMV EFLFDTGLNI EFFGNAREKQ FKNPKYPWTK
APVFTGKIPM NMVSEKNSQA IAALIIGDKN YNDNFITLRV WETMASDAVM
LIDEEFDTKH RIINDARFYV NNRAELIDRV NELKHSDVLR KEMLSIQHDI
LNKTRAKKAE WQDAFKKAID L

METHODS AND KITS FOR DETECTION OF 5-HYDROXYMETHYLCYTOSINE

CROSS-REFERENCE TO RELATED APPLICATIONS

This application claims priority to U.S. Provisional Patent Application No. 61/405,706, filed Oct. 22, 2010, the contents of which are incorporated by reference in its entirety.

FIELD OF THE INVENTION

The present invention relates to methods and kits for the detection of 5-hydroxymethylcytosine (5hmC). In some embodiments, the present invention relates to methods and kits for detection of 5hmC in nucleic acid (e.g., DNA, RNA). In some embodiments, the present invention relates to detection of 5hmC in genomic DNA, e.g., mammalian genomic DNA.

BACKGROUND OF THE INVENTION

DNA methylation consisting of a cytosine modified by a methyl group at the N5 position (5meC) is a well described modification affecting gene expression in mammalian cells. The 5meC modification generally occurs at the CpG dinucleotide sequence; however, it has been identified elsewhere in the genome (Illingworth et al. (2009) FEBS Letters 583:1713-1720; herein incorporated by reference in its entirety). Another type of gene-regulatory DNA modification has more recently been described, 5-hydroxymethylcytosine (5hmC) (Tahiliani et al. (2009) Science 324:930-935; Kriaucionis et al. (2009) Science 324:929-930; each herein incorporated by reference in its entirety). Tahiliani et al. demonstrated that the enzyme Tet1, an iron-dependent α-ketogluterate dioxygenase, catalyzes the formation of 5hmC from 5meC (Tahiliani et al. (2009) Science 324:930-935; herein incorporated by reference in its entirety). Furthermore, the 5hmC base may be an intermediate in the conversion of 5meC to cytosine, thus identifying an enzyme that can potentially demethylate DNA (Tahiliani et al. (2009) Science 324:930-935; herein incorporated by reference in its entirety). 5hmC is a stable DNA modification found in specialized nondividing neurons and in all animal tissues studied to date (Kriaucionis et al. (2009) Science 324:929-930; herein incorporated by reference in its entirety). Intriguingly, 5hmC was not detected in cancerous cell lines. The inability to detect 5hmC in cancerous cell lines indicates that lack of 5hmC may be associated with tumorigenesis. The involvement of 5hmC in epigenetic regulation has been experimentally verified by Jin et al., who showed that 5hmC in DNA inhibits binding of several methyl-CpG-binding domain proteins (Jin et al. (2010) Nucleic Acids Res. 38:e125; Hendrich et al. (1998) Mol. Cellular Biol. 18:6538-6547; each herein incorporated by reference in its entirety). Tet2 and Tet3 also catalyze the formation of 5hmC (Ito et al. (2010) Nature 466:1129-1133; herein incorporated by reference in its entirety). Additionally, the total level of 5hmC present in several mammalian tissues has been quantified (Szwagierczak et al. (2010) Nucleic Acids Res. (advanced online publication); Munzel et al. (2010) Angewandte Chemie Intl. Ed. 49:5375-5377; each herein incorporated by reference in its entirety). However, specific genomic locations of 5hmC remain unknown.

The identification of specific genomic regions containing 5hmC is technically challenging. The most frequently used method for identifying 5meC, bisulfite sequencing, cannot distinguish 5meC from 5hmC (Nestor et al. (2010) Biotechniques 48:317-319; herein incorporated by reference in its entirety). Furthermore, commercially available antibodies raised against 5hmC cannot distinguish between 5meC and 5hmC (Ito et al. (2010) Nature 466:1129-1133; herein incorporated by reference in its entirety). Using polymerase kinetics, one group has been able to differentiate between 5meC and 5hmC (Flusberg et al. (2010) Nature Methods 7:461-465; herein incorporated by reference in its entirety). However, this method is impractical for identification of the 5hmC status of individual genes (Flusberg et al. (2010) Nature Methods 7:461-465; herein incorporated by reference in its entirety).

Improved methods for detecting 5-hydroxymethylcytosine residues in DNA are needed. In particular, improved methods for identifying the level of 5hmC modification at specific regions (e.g., specific gene loci) are needed.

SUMMARY OF THE INVENTION

The present invention relates to methods and kits for the detection of 5-hydroxymethylcytosine (5hmC). In some embodiments, the present invention relates to methods and kits for detection of 5hmC in nucleic acid (e.g., DNA, RNA). In some embodiments, the present invention relates to detection of 5hmC in genomic DNA, e.g., mammalian genomic DNA.

5-hydroxymethylcytosine (5hmC) has been identified in mammalian genomic DNA. Identifying the genomic location of this modified base is of interest for research and diagnostic purposes (e.g., tumor detection). In experiments conducted during the course of developing some embodiments of the present invention, a method was developed for the rapid and inexpensive identification of genomic regions containing 5hmC. In some embodiments, this method involves the selective glucosylation of 5hmC residues by the β-glucosyltransferase from T4 bacteriophage creating β-glucosyl-5-hydroxymethylcytosine (β-glu-5hmC). In some embodiments, the β-glu-5hmC modification provides a target which can be efficiently and selectively pulled down by J-binding protein 1 coupled to magnetic beads. In some embodiments, DNA that is precipitated is suitable for analysis by quantitative PCR, microarray, sequencing, or other techniques. The methods described herein find use in e.g., research, clinical diagnostics, screening assays, etc. In one non-limiting example, methods of the present invention find use in studying the temporal and spatial effects that 5hmC may have on epigenetic regulation at the single gene level. In another non-limiting example, methods of the present invention find use in identifying regions (e.g., tissues, cells) with increased or decreased levels of 5hmC residues relative to a second region, e.g., as an indication of differential biological state (e.g., neoplastic state, tumor development, etc.).

Methods of the present invention are not limited by the sample type to which they are applied. In some preferred embodiments, the sample is a biological sample. The biological sample may be cellular (e.g., tumor sample, biopsy sample, organ sample, tissue sample, bone sample, etc.), or a biological fluid (e.g., sweat, saliva, urine, urine sediment, blood, semen, tears, cerebrospinal fluid, mucus secretion, milk, interstitial fluid, etc.), or a combination thereof.

Methods of the present invention are not limited by type of subject. In some embodiments, the subject is a mammal. In some preferred embodiments, the mammalian subject is human. Methods of the present invention are not limited by age of the subject, physical attributes or physical state (e.g., medical condition) of the subject.

In some preferred embodiments, the sample is exposed to an agent capable of transferring a moiety to 5hmC and thereby "tagging" it. In some preferred embodiments, the agent capable of transferring a moiety to 5hmC is an enzyme. In some particularly preferred embodiments, the enzyme is a glycosyltransferase and the moiety is a carbohydrate (e.g., monosaccharide). Methods of the present invention are not limited by type of glycosyltransferase. The glycosyltransferase may be a glucosyltransfearse, galactosyltransfearse, sialyltransferase, xylosyltransferase, or any other type of glycosyltransferase. In particularly preferred embodiments, the glycosyltransferase is a beta-glucosyltransferase. In particularly preferred embodiments, the beta-glucosyltransferase is a T4 bacteriophage beta-glucosyltransferase.

In some embodiments, the method involves use of an agent that binds to (e.g., recognizes) 5hmC to which a moiety has been added (e.g., glucosylated 5hmC), without limitation to the type or identity of the agent. The agent may be a lectin, an antibody, a J-binding protein, or any other agent (e.g., enzyme, binding protein, nonproteinaceous binding partner) that binds (e.g., noncovalently interacts with) 5hmC to which a moiety has been added (e.g., glucosylated 5hmC). In some embodiments, the association or binding of the agent with the modified (e.g., glycosylated) 5hmC results in direct generation of a detectable signal (e.g., a fluorescent signal, a colorimetric signal). In some embodiments, the association or binding of the agent with the modified (e.g., glycosylated) 5hmC does not result in direct generation of a detectable signal.

In some embodiments, the method further comprises isolation of bound and/or modified 5hmC without limitation to the technique(s) used for such isolation. In some embodiments, an agent capable of binding to a modified 5hmC (e.g., a J binding protein capable of binding to glucosylated 5hmC) is immobilized on a solid substrate without limitation to the type of substrate. Examples of solid substrates include beads, gels, agar, agarose, resins, particles, magnetic particles, paramagnetic particles, impermeable surfaces (e.g., slides, wells (e.g., wells of microtiter plates), chips (e.g., array chips), etc). In some preferred embodiments, immobilization of an agent capable of binding to a modified 5hmC facilitates isolation (e.g., pull-down, sedimentation) of the modified 5hmC residues.

In some embodiments, modified 5hmC (e.g., glucoslated 5hmC) is subjected to further analysis techniques, e.g., for the purpose of quantifying the amount of 5hmC present in a sample. Methods of the present invention are not limited by the type(s) of downstream analysis techniques. Analytical methods include, but are not limited to, PCR, real-time PCR, mass spectrometry techniques, FRET, scintillation counting, sequencing, array analysis (e.g., microarray, gene chip, Affymetrix array), colorimetric assay, enzymatic assay, etc.

Methods of the present invention find use in diagnostic or risk assessment tests, in research (e.g., genetics research, cell biology research, medical research, developmental research), in expression analyses, in drug screening assays, and the like. Methods of the present invention are not limited by the biological state correlated with level of 5hmC detected. Such biological states include, but are not limited to, cancer, autoimmune disorders (e.g., diabetes, rheumatoid arthritis, allergies), genetic and epigenetic diseases, environmentally-mediated conditions, and metabolic conditions.

The present invention provides kits for the detection of 5hmC in a sample. Kit components may include, but are not limited to, buffers, enzymes (e.g., glycosyltransferases, T4 bacteriophage beta-glucosyltransferase, binding proteins, J-binding protein 1), substrates (e.g., glucose), tubes, vessels, containers, beads, resins, magnets, instructions, and the like.

In certain embodiments, the present invention provides a method for detecting 5-hydroxymethylcytosine in a sample comprising: a) obtaining a sample, b) exposing the sample to a glycosyltransferase under conditions that facilitate activity of the glycosyltransferase, and c) contacting the sample exposed to the glycosyltransferase with an agent such as a J-binding protein or an antibody. In some embodiments, the sample is a biological sample. In some embodiments, the biological sample is obtained from a mammal. In some embodiments, the mammal is human. In some embodiments, the glycosyltransferase is a glucosyltransferase. In some embodiments, the glucosyltransferase is a beta-glucosyltransferase. In some embodiments, the beta-glucosyltransferase is a T4 bacteriophage beta-glycosyltransferase. In some embodiments, the agent is a J-binding protein. In some embodiments, the J-binding protein is *Crithidia fasciculate* J-binding protein 1. In some embodiments, the sample comprises nucleic acid. In some embodiments, the nucleic acid is DNA. In some embodiments, the agent is immobilized to a solid substrate. In some embodiments, the solid substrate is a type such as a particulate material or a nonporous material. In some embodiments, the particulate material is a type such as a bead, a colloid, a gel, or a magnetic particle. In some embodiments, the nonporous material is a type such as a well, a plate, or a membrane. In some embodiments, the method further comprises additional step d) isolating the agent immobilized to the solid substrate to generate purified sample. In some embodiments, the method further comprises determining the amount of nucleic acid present in the purified sample. In some embodiments, the determining occurs through a such as PCR, real-time PCR, mass spectrometry, hybridization, gene arrays, or DNA sequencing.

In certain embodiments, the present invention provides a kit for detecting 5-hydroxymethylcytosine in a sample, the kit comprising a glycosyltransferase and an agent such as a J-binding protein or an antibody. In some embodiments, the glycosyltransferase is a beta-glucosyltransferase. In some embodiments, the beta-glucosyltransferase is a T4 bacteriophage beta-glucosyltransferase. In some embodiments, J-binding protein is *Crithidia fasciculate* J-binding protein 1.

Additional embodiments will be apparent to persons skilled in the relevant art based on the teachings contained herein.

DESCRIPTION OF THE DRAWINGS

FIG. 6 provides the amino acid sequence of *Crithidia fasciculate* JBP-1 (SEQ ID NO:1).

FIG. 7 provides the amino acid sequence of T4,3-glucosyltransferase (SEQ ID NO:2).

DEFINITIONS

Figure 1:
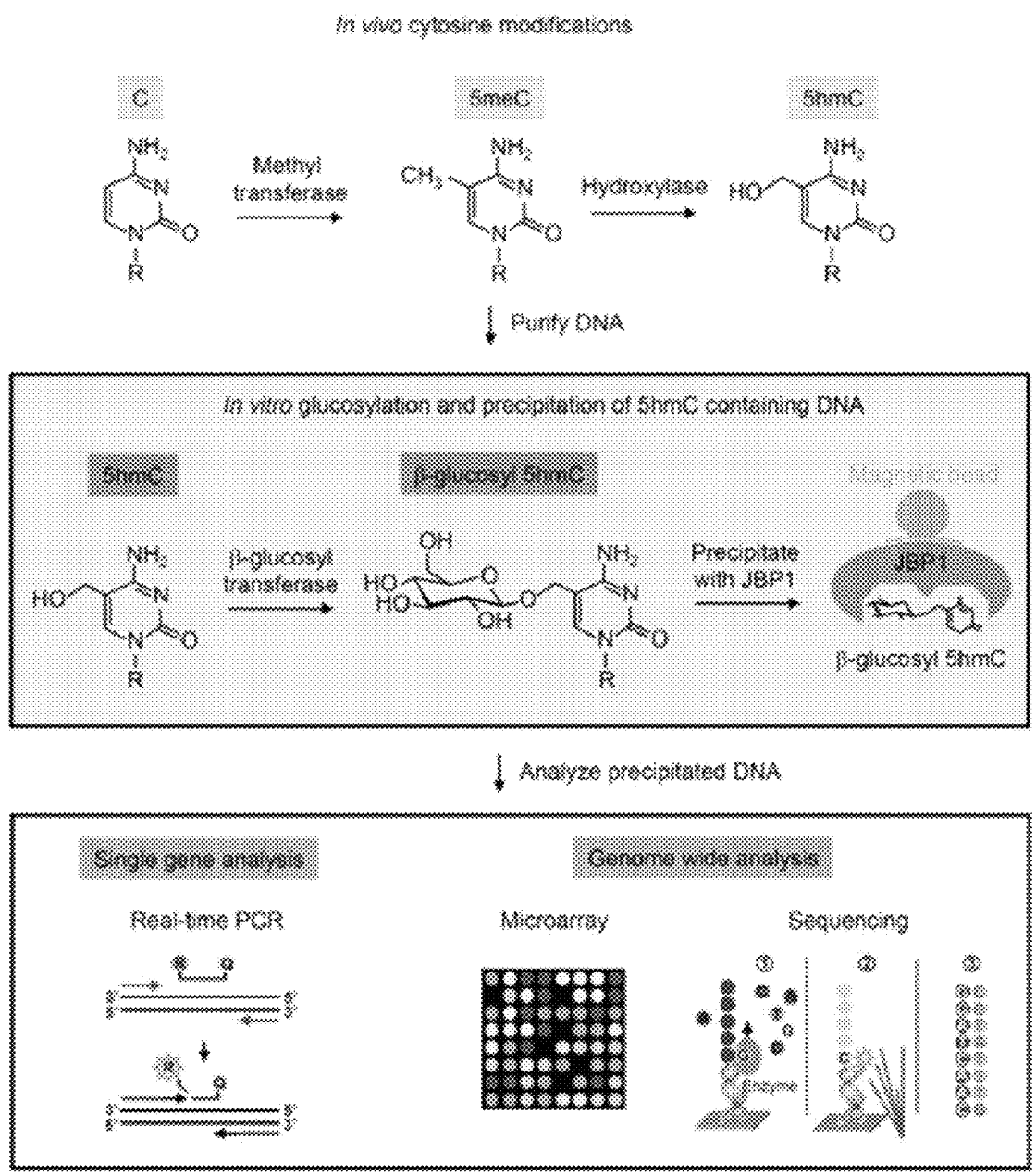
FIG. 1 shows a scheme for the selective pull down of 5hmC. The top panel shows naturally occurring cytosine modifications in mammalian cells. The middle panel gives an overview of the method used to specifically identify 5hmC bases in genomic DNA. The bottom panel shows some applications that can be employed using this method of identifying 5hmC regions.

To facilitate an understanding of the present invention, a number of terms and phrases are defined below:

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (e.g., epigenetic marker; e.g., 5hmC at one or more particular locations) in a positive sample.

As used herein, the term "CpG island" refers to a genomic DNA region that contains a high percentage of CpG sites relative to the average genomic CpG incidence (per same species, per same individual, or per subpopulation (e.g., strain, ethnic subpopulation, or the like). Various parameters and definitions for CpG islands exist; for example, in some embodiments, CpG islands are defined as having a GC percentage that is greater than 50% and with an observed/expected CpG ratio that is greater than 60% (Gardiner-Garden et al. (1987) J Mol. Biol. 196:261-282; Baylin et al. (2006) Nat. Rev. Cancer 6:107-116; Irizarry et al. (2009) Nat. Genetics 41:178-186; each herein incorporated by reference in its entirety). In some embodiments, CpG islands may have a GC content>55% and observed CpG/expected CpG of 0.65 (Takai et al. (2007) PNAS 99:3740-3745; herein incorporated by reference in its entirety). Various parameters also exist regarding the length of CpG islands. As used herein, CpG islands may be less than 100 bp; 100-200 bp, 200-300 bp, 300-500 bp, 500-750 bp; 750-1000 bp; 100 or more by in length. In some embodiments, CpG islands show altered methylation patterns (e.g., altered 5hmC patterns) relative to controls (e.g., altered 5hmC methylation in cancer subjects relative to subjects without cancer; tissue-specific altered 5hmC patterns; altered 5hmC patterns in biological samples from subjects with a neoplasia or tumor relative to subjects without a neoplasia or tumor. In some embodiments, altered methylation involves increased incidence of 5hmC. In some embodiments, altered methylation involves decreased incidence of 5hmC.

As used herein, the term "CpG shore" or "CpG island shore" refers to a genomic region external to a CpG island that is or that has potential to have altered methylation (e.g., 5hmC) patterns (see, e.g., Irizarry et al. (2009) Nat. Genetics 41:178-186; herein incorporated by reference in its entirety). CpG island shores may show altered methylation (e.g., 5hmC) patterns relative to controls (e.g., altered 5hmC in cancer subjects relative to subjects without cancer; tissue-specific altered 5hmC patterns; altered 5hmC in biological samples \from subjects with neoplasia or tumor relative to subjects without neoplasia or tumor. In some embodiments, altered methylation involves increased incidence of 5hmC. In some embodiments, altered methylation involves decreased incidence of 5hmC. CpG island shores may be located in various regions relative to CpG islands (see, e.g., Irizarry et al. (2009) Nat. Genetics 41; 178-186; herein incorporated by reference in its entirety). Accordingly, in some embodiments, CpG island shores are located less than 100 bp; 100-250 bp; 250-500 bp; 500-1000 bp; 1000-1500 bp; 1500-2000 bp; 2000-3000 bp; 3000 bp or more away from a CpG island.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body.

As used herein, "an individual is suspected of being susceptible to metastasized cancer" is meant to refer to an individual who is at an above-average risk of developing metastasized cancer. Examples of individuals at a particular risk of developing cancer of a particular type (e.g., colorectal cancer, bladder cancer, breast cancer, prostate cancer) are those whose family medical history indicates above average incidence of such cancer type among family members and/or those who have already developed cancer and have been effectively treated who therefore face a risk of relapse and recurrence. Other factors which may contribute to an above-average risk of developing metastasized cancer which would thereby lead to the classification of an individual as being suspected of being susceptible to metastasized cancer may be based upon an individual's specific genetic, medical and/or behavioral background and characteristics.

The term "neoplasm" as used herein refers to any new and abnormal growth of tissue. Thus, a neoplasm can be a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells.

As used herein, the term "amplicon" refers to a nucleic acid generated using primer pairs. The amplicon is typically single-stranded DNA (e.g., the result of asymmetric amplification), however, it may be RNA or dsDNA.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. In certain embodiments, the primer is a capture primer.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

DETAILED DESCRIPTION OF THE INVENTION

The present invention relates to methods and kits for the detection of 5-hydroxymethylcytosine (5hmC) in samples (e.g., biological samples). In some embodiments, the present invention relates to methods and kits for detection of 5hmC present in nucleic acid (e.g., DNA, RNA). In some embodiments, the present invention relates to detection of 5hmC in genomic DNA, e.g., mammalian or plant genomic DNA.

In experiments conducted during the course of developing some embodiments of the present invention, novel methods were developed for efficient and selective identification of 5hmC modified nucleotides in DNA. The only other method available to recognize the location of 5hmC modifications—using polymerase kinetics—is prohibitively expensive and is only practical for genome wide sequencing rather than analysis of single gene loci (Flusberg et al. (2010) Nature Methods 7:461-465; herein incorporated by reference in its entirety). Furthermore, it is unsuitable for clinical applications (e.g., wherein 5hmC levels, e.g., 5hmC levels at a particular location(s), are determined as indicators of biological state (e.g., disease, risk of disease). No antibodies exist that have been shown to specifically react with 5hmC; to the contrary, commercially available antisera raised against 5hmC cross-reacts significantly with 5meC6. In addition, a 5hmC residue produces similar results as a 5meC residue when bisulfite sequencing is employed to identify these residues (Nestor et al. (2010) Biotechniques 48:317-319; herein incorporated by reference in its entirety), rendering these approaches to identifying 5hmC unusable without significant improvements.

In some embodiments, the present invention provides systems, methods, kits and reagents for purifying or isolated nucleic acid sequences containing 5hmC residues. In further embodiments, the nucleic acid sequences containing 5hmC residues are analyzed and/or identified, for example by PCR, real time PCR, microarray analysis, sequencing, or other methods that determine the sequence, identity or presence of a nucleic acid sequence of interest. In some embodiments, DNA is obtained from a subject. In some embodiments, the DNA isolated by known methods. In some embodiments, the DNA sample is treated by restriction endonucleases to provide nucleic acid sequences of an approximate desired length. In some embodiments, the DNA from a subject is treated with a glycosyltransferase to glycosylate any 5hmC that are present in the sample. This results in a sample containing glycosyl-5hmC bases within the nucleic acid. The glycosyl-5hmC nucleic acid sample is then contacted with a binding protein specific for the glycosyl-5hmC bases within the nucleic acid. A binding protein-glycosyl-5hmC base complex is formed. In some embodiments, nucleic acids containing glycosyl-5hmC bases are separated from other nucleic acid sequences in the sample based on the formation of the binding protein-glycosyl-5hmC base complex.

The present invention is not limited to the use of a particular glycosyl-5hmC binding agent. In some embodiments, the glycosyl-5hmC binding agent is a protein. In some embodiments, the protein is a J-binding protein (JBP). Suitable J binding proteins are described in FIG. 6 and Table 1. Those of skill in the art will recognize that additional known JBPs and those that may be identified in the future may be tested for use with the present invention. Additionally, the present invention encompasses the use of mutated or modified JBPs which can be identified by their percent identity with reference sequences. In some embodiments, the JBP is J-binding protein 1 (JBP1). In some embodiments, the amino acid sequence of the JBP is at least 80%, 90%, 95%, or 99% identical to the sequence of one or more of the JBPs identified in Table 1. In some embodiments, the JBP is *Crithidia fasciculate* JBP-1 (SEQ ID NO:1). In some embodiments, the JBP has an amino acid sequence that is at least 80%, 90%, 95%, or 99% identical to SEQ ID NO:1. The present invention is not limited to the use of particular 5hmc modifying agents. In some embodiments, the 5hmc modifying agent is an enzyme. In some embodiments, the enzyme is a glyosyltransferase. Suitable glycosyltransferases are exemplified in Table 2. Those of skill in the art will recognize that additional known JBPs and those that may be identified in the future may be tested for use with the present invention. Additionally, the present invention encompasses the use of mutated or modified JBPs which can be identified by their percent identity with reference sequences. In some embodiments, the glycosyltrasferase is at least 80%, 90%, 95%, or 99% identical to the sequence of one or more of the glycosyltransferases. In some embodiments, the glycosyltransferase is a T2, T4 or T6 glucosyltransferase, or a Uracil glycosylase. In some embodiments, the glycosyltransferase is an α- or β-glucosyltransferase. In some embodiments, the glucosyltransferase is T4 β-glucosyltransferase (SEQ ID NO:2). In some embodiments, glucosyltransferase is at least 80%, 90%, 95%, or 99% identical to SEQ ID NO:2.

TABLE 1

J-binding Proteins
Some JBP1 homologues

| Expasy Accession Number | Organism | Description |
| --- | --- | --- |
| Q9U6M2 | *Crithidia fasciculata* | JBP1_CRIFA Thymine dioxygenase JBP1 (EC 1.14.11.6) (J-binding protein 1) |
| A4H5X5 | *Leishmania braziliensis* | Thymine dioxygenase JBP1 (EC 1.14.11.6) (J-binding protein 1) |
| A4HU70 | *Leishmania infantum* | Thymine dioxygenase JBP1 (EC 1.14.11.6) (J-binding protein 1) |
| Q4QHM7 | *Leishmania major* | Thymine dioxygenase JBP1 (EC 1.14.11.6) (J-binding protein 1) |
| Q9U6M1 | *Leishmania tarentolae* | Thymine dioxygenase JBP1 (EC 1.14.11.6) (J-binding protein 1) |
| Q4DLX9 | (*Sauroleishmania tarentolae*) *Trypanosoma cruzi* | Thymine dioxygenase JBP1-B (EC 1.14.11.6) (J-binding protein 1B) |
| Q4DBW3 | *Trypanosoma cruzi* | Thymine dioxygenase JBP1-A (EC 1.14.11.6) (J-binding protein 1A) |
| Q9U6M3 | *Trypanosoma brucei brucei* | Thymine dioxygenase JBP1 (EC 1.14.11.6) (J-binding protein 1) |
| D0A9Q3 | *Trypanosoma brucei gambiense* DAL972 | J-binding protein, putative [TbgDal_XI15230] |
| Q4QFY1 | *Leishmania major* | Bifunctional helicase and thymine dioxygenase JBP2 (J-binding protein 2) [Includes: Probable DNA helicase JBP2 (EC protein 2) [Includes: Probable DNA helicase JBP2 (EC 3.6.4.12); Thymine dioxygenase JBP2 (EC 1.14.11.6)] [JBP2] |

A number of methods are suitable for separation of the binding protein-glycosyl-5hmC base complex. In some embodiments, the binding protein is immobilized on a substrate. For example, in some embodiments, the binding protein is covalently attached to a bead, such as a magnetic bead. Nucleic acid sequences containing glycosyl-5hmC bases bind to the binding proteins immobilized on the beads. The beads containing the bound nucleic acid sequences containing glycosyl-5hmC bases can then be washed to remove unbound sequences from the sample and the bound sequences can be analyzed on the beads or eluted from the beads for further analysis. In some embodiments, the binding protein can be covalently attached to a bead or matrix material suitable for use in column chromatography. Samples containing the glycosyl-5hmC bases are applied to columns comprising the beads or matrix. Nucleic acids containing the glycosyl-5hmC bases are bound by the binding protein and retaining on the column, allowing separation from sequences that do not contain glycosyl-5hmC bases. The nucleic acids containing the glycosyl-5hmC bases can then be eluted from the column and further analyzed. In still other embodiments the binding protein may be associated with another protein that allows separation of the complex. For example, the binding protein may be covalently modified with a second binding molecule. Suitable second binding molecules include biotin, avidin, haptens, immunoglobulins and aptamers. In some of these embodiments, a nucleic acid glycosyl-FhmC base-binding protein-second binding molecule complex is formed. The complex can then be isolated by utilizing reagents that specifically bind the second binding molecules, for examples, beads, magnetic beads or columns comprising avidin, biotin, immunoglobulins specific for the selected hapten, or aptamer binding partner.

Methods presented herein ensure that only 5hmC-containing genomic regions are isolated and identified. Given that the β-gt from T4 specifically catalyzes the glucosylation of 5hmC (FIG. 3; Tomaschewski et al. (1985) Nucleic Acids Res. 13:7551-7568; herein incorporated by reference in its entirety) and JBP1 specifically recognizes the resulting β-glu-5hmC base (b), the DNA pulled down by JBP1 is highly enriched in the 5hmC modification. The isolated DNA is then ready for analysis by real-time quantitative PCR, microarray analysis, sequencing by any method (e.g., high-throughput sequencing), or other techniques. The simple and cost-effective method for identifying genomic regions containing 5hmC presented herein finds use for study of the temporal and spatial patterns of 5hmC residues in genomic regions. For example, in some embodiments, the methods of the present are utilized to isolate DNA that contains 5hmc modification and then the isolated DNA is analyzed to determine the sequence or identity of the isolated DNA.

Particular levels (e.g., thresholds, cutoff points) or locations of 5hmC DNA modification may be used that show optimal function with different ethnic groups or sex, different geographic distributions, different stages of disease, different degrees of specificity or different degrees of sensitivity. Particular levels (e.g., thresholds, cutoff points) of 5hmC DNA modification may also be developed which are particularly sensitive to the effect of therapeutic regimens on disease progression. Subjects may be monitored after a therapy and/or course of action to determine the effectiveness of that specific therapy and/or course of action.

In some embodiments, indicators of biological state (e.g., cancer) include, for example, epigenetic alterations. Epigenetic alterations include but are not limited to DNA methylation (e.g., 5hmC DNA modification). In some embodiments, the level (e.g., frequency or score) of 5hmC DNA modification (e.g., increased levels relative to a control, decreased levels relative to a control) is determined without limitation to the technique used for such determining. Methods of the present invention are not limited to particular locations of epigenetic (e.g., 5hmC) alterations (e.g., 5hmC in coding or regulatory regions). Altered 5hmC levels may occur in, for example, CpG islands; CpG island shores; or regions other than CpG islands or CpG island shores. In this regard, the present invention finds use in the determination of a diagnosis and/or prognosis for cancers such as gastric cancer, lung cancer, prostate cancer, pancreatic cancer, and breast cancer. The present invention also finds use in the determination of a diagnosis or prognosis for other diseases such as diabetes. In other embodiments, the methods may be used to screen subjects to determine if administration of a particular drug or treatment is indicated.

In certain embodiments, methods, kits, and systems of the present invention involve determination of 5hmC state of a locus of interest (e.g., in human DNA) (e.g., in human DNA extracted from a tissue sample, from a tumor sample, etc). Any appropriate method can be used to quantitate 5hmC and/or determine the location of the modification. PCR techniques, for example, can be used to determine which residues are modified by 5hmC following isolation of the nucleic acid sequences by the processes described above. PCR reactions can contain, for example, 10 µL of captured DNA, IX PCR buffer, 0.2 mM dNTPs, 0.5 µM sequence specific primers (e.g., primers flanking a CpG island or CpG shore within the captured DNA), and 5 units DNA polymerase (e.g., Amplitaq DNA polymerase from PE Applied Biosystems, Norwalk, Conn.) in a total volume of 50 µl. A typical PCR protocol can include, for example, an initial denaturation step at 94° C. for 5 min, 40 amplification cycles consisting of 1 minute at 94° C., 1 minute at 60° C., and 1 minute at 72° C., and a final extension step at 72° C. for 5 minutes.

In some embodiments, methods of the present invention involve the determination (e.g., assessment, ascertaining, quantitation) of 5hmC modification level of an indicator of a condition of interest, such as a neoplasm (e.g., the 5hmC level of a CpG island or CpG shore in the coding or regulatory region of a gene locus) in a sample. A skilled artisan understands that an increased, decreased, informative, or otherwise distinguishably different 5hmC modification level is articulated with respect to a reference (e.g., a reference level, a control level, a threshold level, or the like). For example, the term "elevated 5hmC level" as used herein with respect to the 5hmC status of a gene locus is any 5hmC level that is above a median 5hmC level in a sample from a random population of mammals (e.g., a random population of 10, 20, 30, 40, 50, 100, or 500 mammals) that do not have a neoplasm (e.g., a cancer) or other condition of interest. Elevated levels of 5hmC modification can be any level provided that the level is greater than a corresponding reference level. For example, an elevated 5hmC level of a locus of interest can be 0.5, 1, 2, 3, 4, 5, 6, 7, 8, 9, 10, or more fold greater than the reference level 5hmC observed in a normal sample. It is noted that a reference level can be any amount. The term "elevated 5hmC score" as used herein with respect to detected 5hmC events in a matrix panel of particular nucleic acid markers is any 5hmC score that is above a median 5hmC score in a sample from a random population of mammals (e.g., a random population of 10, 20, 30, 40, 50, 100, or 500 mammals) that do not have a neoplasm (e.g., a cancer). An elevated 5hmC score in a matrix panel of particular nucleic acid markers can be any score provided that the score is greater than a corresponding reference score. For example, an elevated score of 5hmC in a locus of interest can be 0.5, 1, 2, 3, 4, 5, 6, 7, 8, 9, 10, or more fold greater than the reference 5hmC score observed in a normal sample. It is noted that a reference score can be any amount that is used for comparison.

Similar considerations apply to assays for decreased levels of 5hmC modifications in a sample, target locus, target genomic region and the like. For example, the term "decreased 5hmC level" as used herein with respect to the 5hmC status of a gene locus is any 5hmC level that is below a median 5hmC level in a sample from a random population of mammals (e.g., a random population of 10, 20, 30, 40, 50, 100, or 500 mammals) that do not have a neoplasm (e.g., a cancer). Decreased levels of 5hmC modification can be any level provided that the level is less than a corresponding reference level. For example, a decreased 5hmC level of a locus of interest can be 0.5, 1, 2, 3, 4, 5, 6, 7, 8, 9, 10, or more fold less than the reference level 5hmC observed in a normal sample. It is noted that a reference level can be any amount. The term "decreased 5hmC score" as used herein with respect to detected 5hmC events in a matrix panel of particular nucleic acid markers is any 5hmC score that is below a median 5hmC score in a sample from a random population of mammals (e.g., a random population of 10, 20, 30, 40, 50, 100, or 500 mammals) that do not have a neoplasm (e.g., a cancer). A decreased 5hmC score in a matrix panel of particular nucleic acid markers can be any score provided that the score is greater than a corresponding reference score. For example, a decreased score of 5hmC in a locus of interest can be 0.5, 1, 2, 3, 4, 5, 6, 7, 8, 9, 10, or more fold less than the reference 5hmC score observed in a normal sample. It is noted that a reference score can be any amount that is used for comparison.

The methods are not limited to a particular type of mammal. In some embodiments, the mammal is a human. In some embodiments, the neoplasm is premalignant. In some embodiments, the neoplasm is malignant. In some embodiments, the neoplasm is cancer without regard to stage (e.g., stage I, II, III, or IV).

The present invention also provides methods and materials to assist medical or research professionals in determining whether or not a mammal has a neoplasm (e.g., cancer). Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the ratio of 5hmC and/or other markers in a sample, and (2) communicating information about the ratio to that professional, for example.

After the level (e.g., score or frequency) of particular 5hmC modification in a sample is reported, a medical professional can take one or more actions that can affect patient care. For example, a medical professional can record the results in a patient's medical record. In some cases, a medical professional can record a diagnosis of a neoplasia, or otherwise transform the patient's medical record, to reflect the patient's medical condition. In some cases, a medical professional can review and evaluate a patient's entire medical record, and assess multiple treatment strategies, for clinical intervention of a patient's condition. In some cases, a medical professional can record a prediction of tumor occurrence with the reported indicators. In some cases, a medical professional can review and evaluate a patient's entire medical record and assess multiple treatment strategies, for clinical intervention of a patient's condition.

A medical professional can initiate or modify treatment of a neoplasm after receiving information regarding the level (score, frequency) associated with 5hmC level in a patient's urine sample. In some cases, a medical professional can compare previous reports and the recently communicated level (score, frequency) of 5hmC modification, and recommend a change in therapy. In some cases, a medical professional can enroll a patient in a clinical trial for novel therapeutic intervention of neoplasm. In some cases, a medical professional can elect waiting to begin therapy until the patient's symptoms require clinical intervention.

A medical professional can communicate the assay results to a patient or a patient's family. In some cases, a medical professional can provide a patient and/or a patient's family with information regarding neoplasia, including treatment options, prognosis, and referrals to specialists, e.g., oncologists and/or radiologists. In some cases, a medical professional can provide a copy of a patient's medical records to communicate assay results to a specialist. A research professional can apply information regarding a subject's assay results to advance neoplasm research. For example, a researcher can compile data on the assay results, with information regarding the efficacy of a drug for treatment of neoplasia to identify an effective treatment. In some cases, a research professional can obtain assay results to evaluate a subject's enrollment, or continued participation in a research study or clinical trial. In some cases, a research professional can classify the severity of a subject's condition, based on assay results. In some cases, a research professional can communicate a subject's assay results to a medical professional. In some cases, a research professional can refer a subject to a medical professional for clinical assessment of neoplasia, and treatment thereof. Any appropriate method can be used to communicate information to another person (e.g., a professional). For example, information can be given directly or indirectly to a professional. For example, a laboratory technician can input the assay results into a computer-based record. In some cases, information is communicated by making a physical alteration to medical or research records. For example, a medical professional can make a permanent notation or flag a medical record for communicating a diagnosis to other medical professionals reviewing the record. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

It is noted that a single sample can be analyzed for one neoplasm-specific marker or for multiple neoplasm-specific markers. In preferred embodiments, a single sample is analyzed for multiple neoplasm-specific markers, for example, using multi-marker assays. In addition, multiple samples can be collected for a single mammal and analyzed as described herein. In some embodiments, a sample is split into first and second portions, where the first portion undergoes cytological analysis and the second portion undergoes further purification or processing (e.g., sequence-specific capture step(s) (e.g., for isolation of specific loci for analysis of 5hmC levels). In some embodiments, the sample undergoes one or more preprocessing steps before being split into portions. In some embodiments, the sample is treated, handled, or preserved in a manner that promotes DNA integrity and/or inhibits DNA degradation (e.g., through use of storage buffers with stabilizing agents (e.g., chelating agents, DNase inhibitors) or handling or processing techniques that promote DNA integrity (e.g., immediate processing or storage at low temperature (e.g., −80 degrees C.)).

In some embodiments, all the basic essential materials and reagents required for detecting neoplasia through detecting both the level (presence, absence, score, frequency) of markers in a sample obtained from the mammal are assembled together in a kit. Such kits generally comprise, for example, reagents useful, sufficient, or necessary for detecting and/or characterizing one or more markers (e.g., epigenetic markers; 5hmC modifications) specific for a neoplasm. In some embodiments, the kits contain enzymes suitable for amplifying nucleic acids including various polymerases, deoxynucleotides and buffers to provide the necessary reaction mixture for amplification. In some embodiments, the kits of the present invention include a means for containing the reagents in close confinement for commercial sale such as, e.g., injection or blow-molded plastic containers into which the desired reagent are retained. Other containers suitable for conducting certain steps of the disclosed methods also may be provided.

In some embodiments, the methods disclosed herein are useful in monitoring the treatment of neoplasia (e.g., cancer). For example, in some embodiments, the methods may be performed immediately before, during and/or after a treatment to monitor treatment success. In some embodiments, the methods are performed at intervals on disease free patients to ensure treatment success.

The present invention also provides a variety of computer-related embodiments. Specifically, in some embodiments the invention provides computer programming for analyzing and comparing a pattern of neoplasm-specific marker detection results in a sample obtained from a subject to, for example, a library of such marker patterns known to be indicative of the presence or absence of a neoplasm, or a particular stage or neoplasm.

In some embodiments, the present invention provides computer programming for analyzing and comparing a first and a second pattern of neoplasm-specific marker detection results from a sample taken at least two different time points. In some embodiments, the first pattern may be indicative of a pre-cancerous condition and/or low risk condition for cancer and/or progression from a pre-cancerous condition to a cancerous condition. In such embodiments, the comparing provides for monitoring of the progression of the condition from the first time point to the second time point.

In yet another embodiment, the invention provides computer programming for analyzing and comparing a pattern of neoplasm-specific marker detection results from a sample to a library of neoplasm-specific marker patterns known to be indicative of the presence or absence of a cancer, wherein the comparing provides, for example, a differential diagnosis between a benign neoplasm, and an aggressively malignant neoplasm (e.g., the marker pattern provides for staging and/or grading of the cancerous condition).

The methods and systems described herein can be implemented in numerous ways. In one embodiment, the methods involve use of a communications infrastructure, for example the internet. Several embodiments of the invention are discussed below. It is also to be understood that the present invention may be implemented in various forms of hardware, software, firmware, processors, distributed servers (e.g., as used in cloud computing) or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

For example, during or after data input by the user, portions of the data processing can be performed in the user-side computing environment. For example, the user-side computing environment can be programmed to provide for defined test codes to denote platform, carrier/diagnostic test, or both; processing of data using defined flags, and/or generation of flag configurations, where the responses are transmitted as processed or partially processed responses to the reviewer's computing environment in the form of test code and flag configurations for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which generally includes test data (e.g., specific gene products assayed), and test result data (e.g., the pattern of neoplasm-specific marker (e.g., epigenetic marker, 5hmC modification) detection results from a sample). This information received can be stored at least temporarily in a database, and data analyzed in comparison to a library of marker patterns known to be indicative of the presence or absence of a pre-cancerous condition, or known to be indicative of a stage and/or grade of cancer.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In some embodiments, all or a portion of the input data and/or all or a portion of the output data (e.g., usually at least the library of the pattern of neoplasm-specific marker detection results known to be indicative of the presence or absence of a pre-cancerous condition) are maintained on a server for access, e.g., confidential access. The results may be accessed or sent to professionals as desired.

A system for use in the methods described herein generally includes at least one computer processor (e.g., where the method is carried out in its entirety at a single site) or at least two networked computer processors (e.g., where detected marker data for a sample obtained from a subject is to be input by a user (e.g., a technician or someone performing the assays)) and transmitted to a remote site to a second computer processor for analysis (e.g., where the pattern of neoplasm-specific marker) detection results is compared to a library of patterns known to be indicative of the presence or absence of a pre-cancerous condition), where the first and second computer processors are connected by a network, e.g., via an intranet or internet). The system can also include a user component(s) for input; and a reviewer component(s) for review of data, and generation of reports, including detection of a pre-cancerous condition, staging and/or grading of a neoplasm, or monitoring the progression of a pre-cancerous condition or a neoplasm. Additional components of the system can include a server component(s); and a database(s) for storing data (e.g., as in a database of report elements, e.g., a library of marker patterns known to be indicative of the presence or absence of a pre-cancerous condition and/or known to be indicative of a grade and/or a stage of a neoplasm, or a relational database (RDB) which can include data input by the user and data output. The computer processors can be processors that are typically found in personal desktop computers (e.g., IBM, Dell, Macintosh), portable computers, mainframes, minicomputers, or other computing devices.

The input components can be complete, stand-alone personal computers offering a full range of power and features to run applications. The user component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe, or distributed across multiple servers (e.g., as in cloud computing applications) and offers data management, information sharing between clients, network administration and security. The application and any databases used can be on the same or different servers. Other computing arrangements for the user and server(s), including processing on a single machine such as a mainframe, a collection of machines, or other suitable configuration are contemplated. In general, the user and server machines work together to accomplish the processing of the present invention.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

The present invention is useful for both the diagnosing diseases and disorders in a subject as well as determining the prognosis of a subject. The methods, reagents and systems of the present invention are applicable to a broad variety of diseases and disorders. In certain embodiments, the present invention provides methods for obtaining a subject's risk profile for developing neoplasm (e.g., cancer). In some embodiments, such methods involve obtaining a sample from a subject (e.g., a human at risk for developing cancer; a human undergoing a routine physical examination), detecting the presence, absence, or level (e.g., 5hmC modification frequency or score) of one or more markers specific for a neoplasm in or associated with the sample (e.g., specific for a neoplasm) in the sample, and generating a risk profile for developing neoplasm (e.g., cancer) based upon the detected level (score, frequency) or presence or absence of the indicators of neoplasia. For example, in some embodiments, a generated risk profile will change depending upon specific markers and detected as present or absent or at defined threshold levels. The present invention is not limited to a particular manner of generating the risk profile. In some embodiments, a processor (e.g., computer) is used to generate such a risk profile. In some embodiments, the processor uses an algorithm (e.g., software) specific for interpreting the presence and absence of specific 5hmC modifications as determined with the methods of the present invention. In some embodiments, the presence and absence of specific markers as determined with the methods of the present invention are inputted into such an algorithm, and the risk profile is reported based upon a comparison of such input with established norms (e.g., established norm for pre-cancerous condition, established norm for various risk levels for developing cancer, established norm for subjects diagnosed with various stages of cancer). In some embodiments, the risk profile indicates a subject's risk for developing cancer or a subject's risk for re-developing cancer. In some embodiments, the risk profile indicates a subject to be, for example, a very low, a low, a moderate, a high, and a very high chance of developing or re-developing cancer. In some embodiments, a health care provider (e.g., an oncologist) will use such a risk profile in determining a course of treatment or intervention (e.g., biopsy, wait and see, referral to an oncologist, referral to a surgeon, etc.).

Other diseases and disorders that may be diagnosed or prognosed with the methods, reagents and systems of the present invention include, but are not limited to, Prader-Willi syndrome, Angelman syndrome, Beckwith-Wiedemann syndrome, Pseudohypoparathyroidism, Russell-Silver syndrome, ICF syndrome, Rett syndrome, α-thalassemia/ mental retardation, X-linked (ATR-X), Immunoosseous dysplasia, Schimke type, Rubinstein-Taybi syndrome, MTHFR deficiency, Recurrent hydatidiform mole, Fragile X mental retardation syndrome, Deletion LCR γδβ- and δβ-thalassemia, FSH dystrophy, disorders of XIC, Schimke immunoosseous dysplasia (SIOD), Sotos syndrome, Atrichia, X-linked Emery-Dreifuss muscular dystrophy (EDMD), Autosomal EDMD, CMT2B1, mandibuloacral dysplasia, limb-girdle muscular dystrophy type 1B, familial partial lipodystrophy, dilated cardiomyopathy 1A, Hutchinson-Gilford progeria syndrome, and Pelger-Huet anomaly.

The following examples are provided in order to demonstrate and further illustrate certain preferred embodiments and aspects of the present invention and are not to be construed as limiting the scope thereof.

EXAMPLE 1

Efficient and Selective Identification of 5-hydroxymethylcytosine in Genomic DNA Materials and Methods
Protein Purifications
β-glucosyltransferase The bgt gene was amplified from T4 bacteriophage DNA and was cloned into pET28a. Cultures of Rosetta(DE3) pLysS harboring pET28a-bgt were grown in 500 ml Studier auto-inducing media$_{20}$ to an $A_{600}$ of 0.6 at 37° C. followed by a shift to 18° C. for 20 hrs. The cells were harvested by centrifugation and suspended in 10 ml β-gt lysis buffer (500 mM NaCl, 25 mM Hepes KOH (pH 7.9), 5 mM imidazole, 10% (v/v) glycerol). All subsequent steps were carried out at 4° C. unless otherwise specified.

After suspension in lysis buffer, cells were incubated for 1 hr with lysozyme added to a final concentration of 200 ug/ml. After 1 hr Triton-X100 was added to the lysate to a final concentration of 0.1% (v/v) and the lysate was heated briefly to 20° C. The lysate viscosity was reduced by sonication on ice. The lysate was clarified by centrifugation for 60 min at 20,000 rpm in a SS34 rotor (Sorvall). After centrifugation the supernatant was applied and batch bound for 1 hr to 2 ml of Talon Resin (GE Healthcare) equilibrated in β-gt lysis buffer. The lysate was applied to a column and washed with β-gt lysis buffer until the flow through had had an $A_{280}$ of 0. β-gt was eluted with 20 ml β-gt lysis containing 200 mM imidazole.

Fractions containing the highest concentration of protein were pooled and dialyzed 3 times against 100 volumes of β-gt low salt buffer (50 mM NaCl, 25 mM Hepes KOH (pH 7.9), 0.5 mM EDTA (pH 8.0), 10% (v/v) glycerol). The pool was then applied to a Resource S cation exchange column. The column was eluted with a 50 to 500 mM linear NaCl gradient. Relevant fractions were pooled and dialyzed against 100 volumes β-gt storage buffer (250 mM NaCl, 25 mM Hepes KOH (pH 7.9), 1 mM EDTA (pH 8.0), 50% (v/v) glycerol).

J-Binding Protein 1

The gene encoding J-binding protein 1 (JBP1) from *C. fasciculata* was synthesized by GeneArt (Germany). After synthesis the gene was cloned into pET28a. Cultures of Rosetta(DE3)pLysS harboring pET28a-JBP1 were grown in 500 ml Studier auto-inducing media to an OD $A_{600}$ of 0.6 at 37° C. followed by a shift to 18° C. for 20 hrs. The cells were harvested by centrifugation and suspended in 10 ml JBP1 lysis buffer (500 mM NaCl, 25 mM Tris HCl (pH 7.5), 5 mM imidazole, 10% (v/v) glycerol). All subsequent steps were carried out at 4° C. unless otherwise specified.

After suspension in JBP1 lysis buffer, cells were incubated for 1 hr with lysozyme added to a final concentration of 200 ug/ml. After 1 h, Triton-X100 was added to the lysate to a final concentration of 0.1% (v/v) and the lysate was heated briefly to 20° C. The lysate viscosity was reduced by sonication on ice. The lysate was clarified by centrifugation for 10 min at 10,000 rpm in a SS34 rotor (Sorvall). After centrifugation the supernatant was applied and batch bound for 1 hr to 2 ml of Talon Resin (GE Healthcare) equilibrated in JBP1 lysis buffer. The lysate was applied to a column and washed with JBP1 lysis buffer until the flow through had an OD $A_{280}$ of 0. JBP1 was eluted with 20 ml JBP1 lysis buffer containing 200 mM imidazole. Fractions containing the highest concentration of protein were pooled and concentrated to 500 µl using a centricon MWCO 30000 according to the manufacturer's instructions. The concentrated protein was applied to a Superdex75 size exclusion column and eluted with JBP1 Superdex Buffer (250 mM NaCl, 25 mM Tris HCl (pH 7.5), 1 mM EDTA (pH 8.0), 1 mM DTT, 10% (v/v) glycerol. Fractions containing no detectable contaminants (as judged by SDS-PAGE) were pooled and 3 times dialyzed against 100 volumes PBS (150 mM NaCl, 50 mM $KPO_4$ (pH 7.2)).

Coupling JBP1 to Magnetic Beads

Five milligrams of Epoxy modified magnetic beads (Dynal, Oslo, Norway) were equilibrated according to the manufacturer's instructions and suspended in 60 µl PBS. 100 µg of JBP1 in PBS was added to the beads and the PBS was added until the volume equalled 120 µl, followed by the addition of 40 µl 4 M $(NH_4)_2SO_4$. The bead/JBP1 solution was slowly rotated at 4° C. for 48 h. After incubation, the protein not bound to the beads was removed and binding efficiencies were calculated (typical binding efficiencies were between 70-80%). The beads were then blocked with 300 µl binding buffer (2 mM EDTA (pH 8.0), 10 mM Tris (pH 8.0), 150 mM NaCl, 0.02% (v/v) Tween 20, 1 mg/ml BSA). After blocking beads were washed 3 times with 300 µl binding buffer and finally suspended in 300 µl binding buffer. Beads were prepared freshly for each experiment as it was found that several freeze thaw cycles dramatically reduced binding capacity.

Substrates

Oligonucleotide Substrates

Annealing reactions (50 µl) containing 100 pmol of each complementary oligonucleotide, 40 mM Tris-HCl (pH 7.5), 10 mM $MgCl_2$, 1 mM dithiothreitol, 50 mM NaCl were heated to 95° C. in a thermocycler for 5 minutes followed decrease in temperature of 1° C./min to 25° C. Duplex oligonucleotides were then purified from a 15% nondenaturing PAGE according to the protocol established by Sambrook et al ((1989) Molecular Cloning, a Laboratory Manual, $2^{nd}$ Ed., Cold Spring Harbor Laboratory Press).

PCR Amplified Substrates

Substrates containing cytosine residues or 5meC residues were amplified from pUC18 or from specific mouse genomic regions using a PCR reaction containing unmodified dNTPs with Pfu Turbo (Stratagene) according to the manufacturer's instructions. 5meC residues were created by incubating the PCR product amplified using unmodified dNTPs with M. SssI methyltransferase (NEB) according to the manufacturer's instructions. Substrates containing 5hmC residues or β-glu-5hmC residues were amplified as other substrates except that d5hmCTP (Bioline) was used in place of dCTP. β-glu-5hmC substrates were generated by incubating the PCR product created using d5hmCTP with 10 µg β-gt, 20 µM UDP-glucose (Sigma) in β-gt reaction buffer (20 mM $KPO_4$ (pH 8.0), 25 mM $MgCl_2$). Substrates were purified on a 0.8% agarose gel and excised using a gel extraction kit (Qiagen).

Radiolabeled Substrates

Reactions (50 µl) containing 1 µg DNA substrate, 10 µCi γ-[$_{32}$P]ATP, 2.5 units T4 polynucleotide kinase (NEB) and buffer supplied by the manufacturer were incubated at 37° C. for 30 min. After 30 min 100 µmol ATP was added and the reaction was allowed to proceed for 10 min. Enzyme and free nucleotide was removed using a nucleotide removal kit (Qiagen).

β-gt Specificity and Activity Assay

Reactions (50 µl) containing 1 pmol double stranded oligonucleotide substrate, 20 Mm UDP-Glucose, 10 µg β-gt, and β-gt reaction buffer were incubated at 37° C. for 60 min. Reactions were terminated by the addition of 10 µl Stop Buffer (20 µg Proteinase K, 50 mM Tris HCl (pH 8.0), 100 mM EDTA (pH 8.0), 2% (w/v) SDS) followed by incubation at 42° C. for 60 min. Oligonucleotides were purified by phenol:$CHCl_3$:IAA extraction followed by an ethanol precipitation. Pellets were suspended in 50 µl NEB buffer 4 and 10 units TaqI (NEB) and were allowed to incubate at 65° C. for 16 hrs. TaqI was inactivated by heating to 80° C. for 20 min followed by incubation with 2.5 units of shrimp alkaline phosphatase (NEB) for 30 min. The alkaline phosphatase was inactivated by heating to 65° C. for 5 min. Reactions were radiolabeled by adding 2.5 units T4 polynucleotide kinase, 10 µCi γ-[$_{32}$P]-ATP, and the volume was raised to 70 µl with T4 polynucleotide kinase buffer. DNA was cleaned by phenol:$CHCl_3$:IAA (isoamyl alcohol) extraction followed by an ethanol precipitation. Pellets were suspended in 5 µl DNase I buffer and 0.2 units DNase I (NEB) and 0.2 units snake venom phosphodiesterase (Worthington) was added to the reactions. Reactions were incubated at 25° C. for at least 4 hours. 0.5 µl of each reaction was spotted onto a 100 µm×20 cm×20 cm cellulose thin layer plate. The nucleotides were resolved in two phases: the first phase contained isobutyric acid:water:$NH_3$ (66:20:1) the second phase contained 4 M ammonium sulfate:1 M acetic acid: isopropanol (80:17:2). Radioactive spots were identified using a phosphor screen.

LC/MS/MS Analysis

DNA substrates were composed of 2.7 kb linear pUC18 PCR products that contained only cytosines, 5meC at CpG regions, only 5hmC, or were treated with 100 ng β-gt in the presence of 20 µM UDP-glucose created as described above. Substrates were hydrolyzed to nucleosides by incubation with nuclease P1, snake venom phosphodiesterase, and alkaline phosphatase (Sigma-Aldrich, St. Louis, Mo.) as described (Crain (1990) Methods Enzymol. 193:782-790; herein incorporated by reference in its entirety). Three volumes of methanol were added to the reactions after digestion was completed and the reactions were centrifuged at 16,000 g for 30 min. The supernatants were dried under vacuum and the resulting residues were dissolved in 50 µl 5% (v/v) methanol for analysis by LC/MS/MS. Chromatographic separation of nucleosides was performed using a Shimadzu Prominence HPLC system with a Zorbax SB-C18 2.1×150 mm i.d. (3.5 µm) reverse phase column equipped with a Eclipse XDB-C8 2.1×12.5 mm i.d. (5 µm) guard column (Agilent Technologies, USA), with a flow rate of 0.2 ml/min at ambient temperature. The mobile phase consisted of A (0.1% formic acid in water) and B (0.1% formic acid in methanol), starting with 95% A/5% B for 0.5 min, followed by a 6.5-min linear gradient of 5-50% B, 2 min with 50% B and 6 min re-equilibration with the initial mobile phase conditions. Online mass spectrometry detection was performed using an Applied Biosystems/MDS Sciex 5000 triple quadrupole mass spectrometer (Applied Biosystems Sciex, USA) with TurbolonSpray probe operating in positive electrospray ionization mode. The deoxyribonucleosides were monitored by multiple reaction monitoring using the mass transitions 228.2→112.1 (dC), 242.2→126.1 (5-me(dC)), 258.2→142.1 (5-hm(dC)), and 420.2→304.1 (5-Gly-hm(dC)).

JBP1 Pull Down Reactions

Pull down reactions (200 µl) containing 132 ng JBP1 coated beads and 10 ng radiolabeled DNA when using PCR amplified substrates or 208 fmol 37mer, binding buffer (2 mM EDTA (pH 8.0), 10 mM Tris HCl (pH 8.0) 150 mM NaCl, 0.02% (v/v) Tween 20, 1 mg/ml BSA) were incubated for 60 min at room temperature with gentle rotation. After incubation the supernatant was collected and counted by scintillation counting. The JBP1 coated beads were washed 3 times with 300 µl binding buffer without BSA. Radioactivity bound to the beads was counted using scintillation counting.

qPCR Varying Bead Concentrations

Reactions (200 µl) contained 10 ng of each DNA substrate combined in one vial, with binding buffer and varying amounts of JBP1 modified magnetic beads were incubated for 60 min at room temperature with gentle rotation. After washing 3 times with 300 µl binding buffer without BSA and the beads were suspended in 90 µl binding buffer and 10 µl stop buffer was added (20 µg/ml Proteinase K, 50 mM Tris HCl (pH 8.0), 100 mM EDTA (pH 8.0), 2% (w/v) SDS) and allowed to incubate at 42° C. for 60 min. After incubation the DNA was cleaned using a PCR clean kit (Qiagen) and the amount of each DNA pulled down relative to the input was measured by quantitative real time PCR.

Complete Glucosylation and Pull Down Assay

Reactions (50 µl) containing 20 ng of each of three DNA substrates (unmodified cytosine, 5meC, 5hmC genomic regions combined in one vial), 20 µM UDP-Glucose, and β-gt reaction buffer, and either 10 µg β-gt or β-gt storage buffer were incubated at 37° C. for 30 minutes. Reactions were stopped by the addition of 10 µl stop buffer. DNA was purified using a PCR clean kit (Qiagen). The cleaned DNA was incubated with 20 µg JBP1 coated magnetic beads in 200 µl binding buffer for 60 minutes with gentle rotation. Beads were washed 3 times with 300 µl binding buffer without BSA and the beads were suspended in 90 µl binding buffer and incubated at 42° C. for 60 min with 10 µl stop buffer. DNA was then cleaned using a PCR clean kit. The amount of each DNA pulled down relative to the input was quantified using real time PCR. The fold enrichment above cytosine was calculated by dividing each pulled down amount by the amount of cytosine containing DNA pulled down.

Results

A brief overview of a scheme of one embodiment of the present invention to specifically identify genomic regions containing 5hmC residues is shown (FIG. 1). Briefly, the β-gt was used to specifically modify 5hmC residues creating β-glu-5hmC residues. Following the complete conversion of 5hmC to β-glu-5hmC, DNA was incubated with JBP1-coated magnetic beads. JBP1 specifically binds β-glu-5hmC containing DNA, allowing for efficient and selective identification of DNA containing 5hmC. The resulting DNA was purified and ready for analysis by various methods.

The β-Glucosyltransferase Specifically Glucosylates 5-Hydroxymethylcytosine

Figure 2:
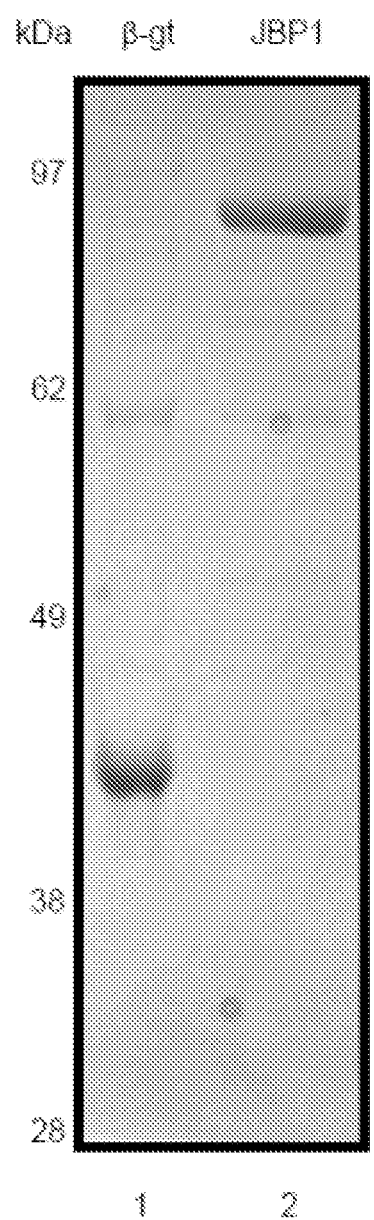
FIG. 2 shows beta-glucosyltransferase (b-gt) and J base binding protein 1 (JBP1 purified to near-homogeneity. Proteins were purified as described herein (Example 1). 3 μg of purified b-gt (lane 1) and 3 μg of JBP1 (lane 2) were loaded onto a 12% SDS-PAGE to assay protein purity.
Figure 3:
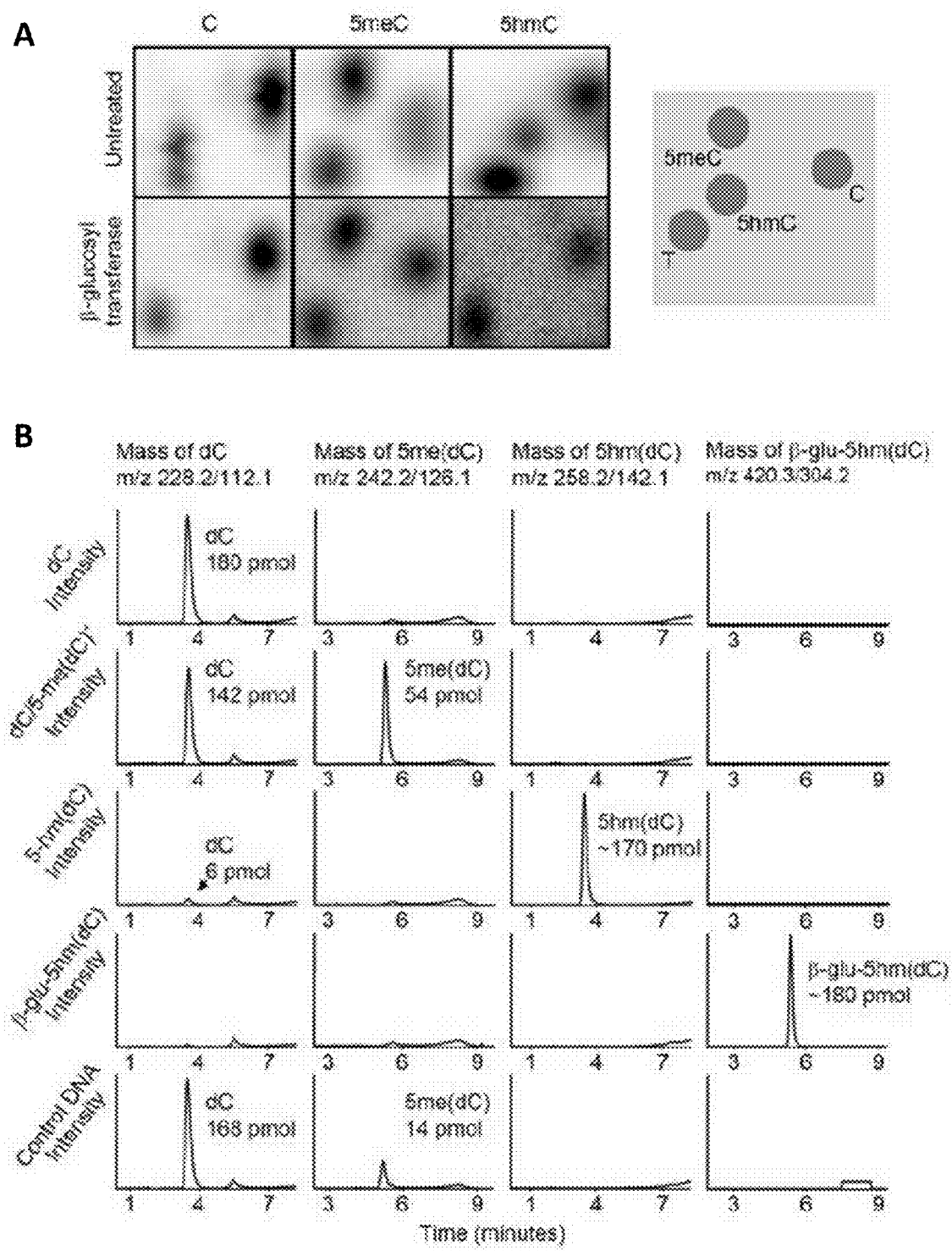
FIG. 3 shows that β-gt can specifically modify 5hmC residues at a high efficiency. (a) Oligonucleotides that were either incubated in the presence or absence of the β-gt were digested with TaqI, treated with alkaline phosphatase, 5'-end labelled using T4 polynucleotide kinase, and digested to 5' mononucleotides using DNase I and Snake Venom Phosphodiesterase. Radiolabelled mononucleotides were analysed by two-dimensional thin-layer chromatography (TLC). Abbreviations: C, 3'-deoxyribocytosine-5'-monophosphate; T, 3'-deoxyribothymidine-5'-monophosphate; 5meC, 3'-deoxyribo-N5-methylcytosine-5'-monophosphate; 5hmC, 3'-deoxyribo-N5-hydroxymethylcytosine-5'-monophosphate. (b) HPLC coupled to tandem mass spectrometry was used to measure the efficiency of the β-gt reaction. Substrates analysed were 2.7 kb linear PCR products of pUC18: the dC substrate contained only cytosine residues; the 5meC substrate was created by methylating the CpG dinucleotide of the cytosine substrate; the 5hmC substrate was created by using d5hmC in place of dCTP in the PCR reactions; the β-glu-5hmC substrate was created by incubating the 5hmC substrate with the β-gt in the presence of UDP-glucose. Control DNA was prepared from salmon sperm. LC/MS/MS chromatograms of the cytosine residues from each of the substrates are presented. Abbreviations: dC, 3'-deoxyribocytosine; 5me(dC), 3'-deoxyribo-N5-methylcytosine; 5hm(dC), 3'-deoxyribo-N5-hydroxymethylcytosine; 5-glu-hm(dC), 3'-deoxyribo-N5-(β-Dglucosyl(hydroxymethyl))cytosine. *Cytosines are only 5meC modified at CpG sequences.
Figure 4:
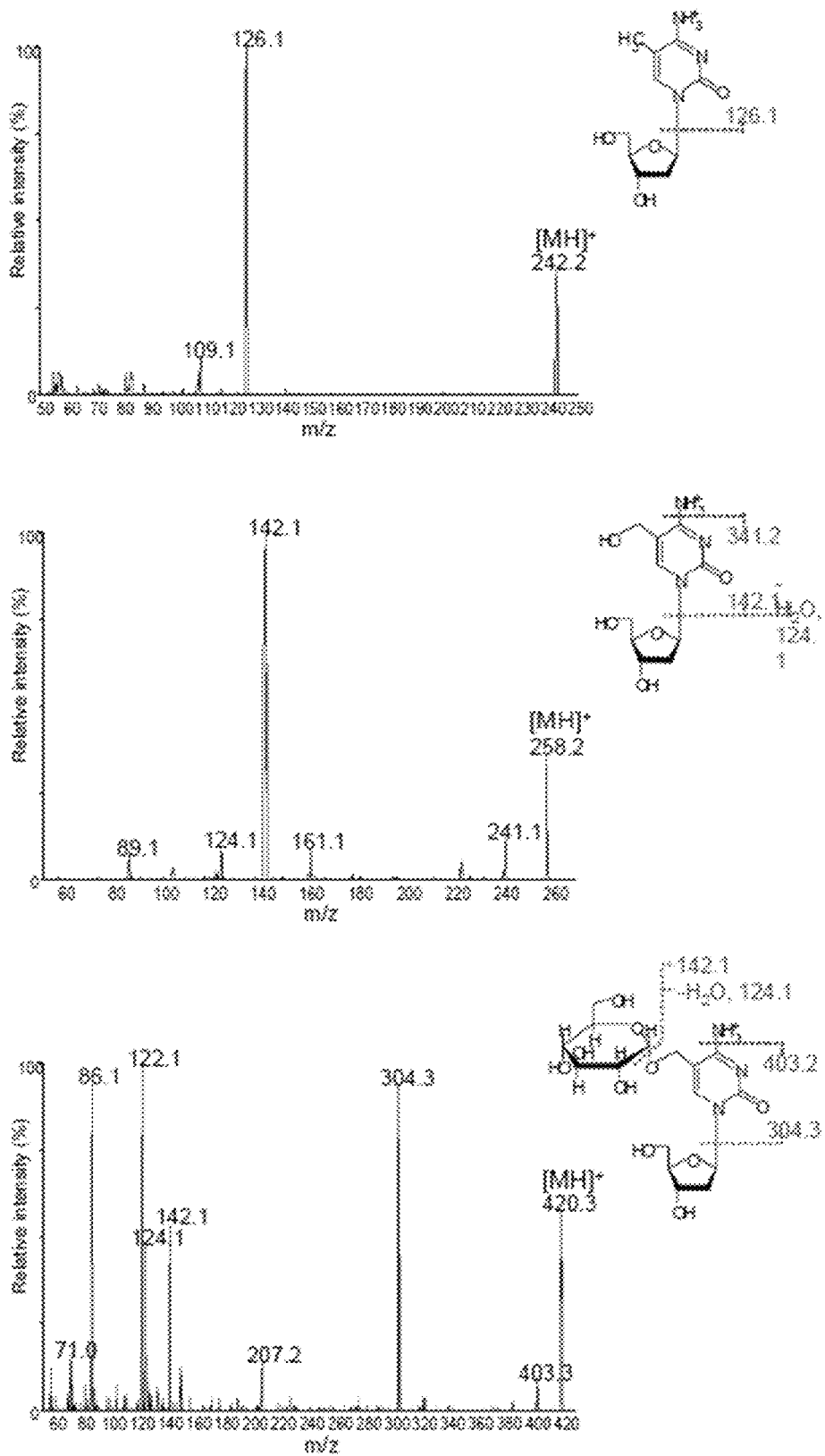
FIG. 4 shows MS/MS product ion spectra of 5-me(dC), 5-hm(dC), and 5-Gly-hm(dC) detected in dsDNA pUC18 PCR products. The spectra were obtained by collision-induced dissociation of the positive precursor ions [MH]$^+$ at m/z 242.2 (5-me(dC)), 258.2 (5-hm(dC)), or 420.3 (5-Gly-hm(dC)). The proposed origins of key fragment ions are as indicated.

Recombinant β-gt from phage T4 was expressed and purified to greater than 90% purity (FIG. 2; lane 1) by Cobalt affinity chromatography, followed by cation exchange chromatography. The β-gt specifically glucosylates 5hmC residues (Tomaschewski et al. (1985) Nucleic Acids Res. 13:7551+7568; Georgopoulos et al. (1971) Virology 44:271-285; Kornberg et al. (1961) J. Biol. Chem. 236:1487-1493; each herein incorporated by reference in its entirety); yet, the efficiency and specificity of the purified enzyme was tested to ensure that the purification scheme resulted in active T4 β-gt. Three double-stranded 37-bp substrates were created: one contained unmodified cytosine at a TaqI restriction site, the second contained 5meC at the TaqI site, and the third contained a 5hmC at the TaqI site. Each of the three substrates was treated with purified β-gt in the presence of UDP-glucose or incubated in the absence of β-gt. The resulting products were digested with TaqI, treated with alkaline phosphatase, 5'-end labelled using T4 polynucleotide kinase, and digested to 5' mononucleotides using DNase I and Snake Venom Phosphodiesterase. The resulting nucleotides were then resolved using two-dimensional thin-layer chromatography (TLC). From the TLC analysis it was deduced that the β-gt has no effect on the substrates that lack 5hmC (FIG. 3; left and center); however, upon treatment with β-gt the 5hmC spot is absent from the TLC plate (FIG. 3; right). This result confirms that the 5hmC has been specifically modified by the β-gt, demonstrating that β-gt is active. The cytosine and thymidine spots are good reference markers and are present because the substrates terminate with 5'-cytosine and 5'-thymidine residues. Additionally, mass spectrometry was performed on each of the substrates to reinforce that the β-gt can modify 5hmC residues at nearly 100% efficiency (FIG. 3b and FIG. 4).

JPB1 from *C. fasciculata* Can Specifically Pull Down β-glucosyl-5hmC

Recombinant *C. fasciculata* JBP1 containing a his-tag was purified to greater than 90% homogeneity by cobalt affinity chromatography followed by size exclusion chromatography. Fractions included in the final pool of purified JBP1 were determined to be free of detectable nucleases (FIG. 2; lane 2). Following purification, JBP1 was covalently linked to epoxy modified magnetic beads as described supra.

JBP1 coated magnetic beads were incubated with four different radiolabeled substrates and precipitated using a magnet. Each substrate was a 2.7 kb linear PCR product created using pUC18 as a template. The substrates contained normal adenines (A), guanines (G) and thymidines (T) and either: only cytosine residues, 5meC residues in CpG sequences, only 5hmC residues, or β-glu-5hmC residues produced by incubating the 5hmC substrate with the β-gt.

Figure 5:
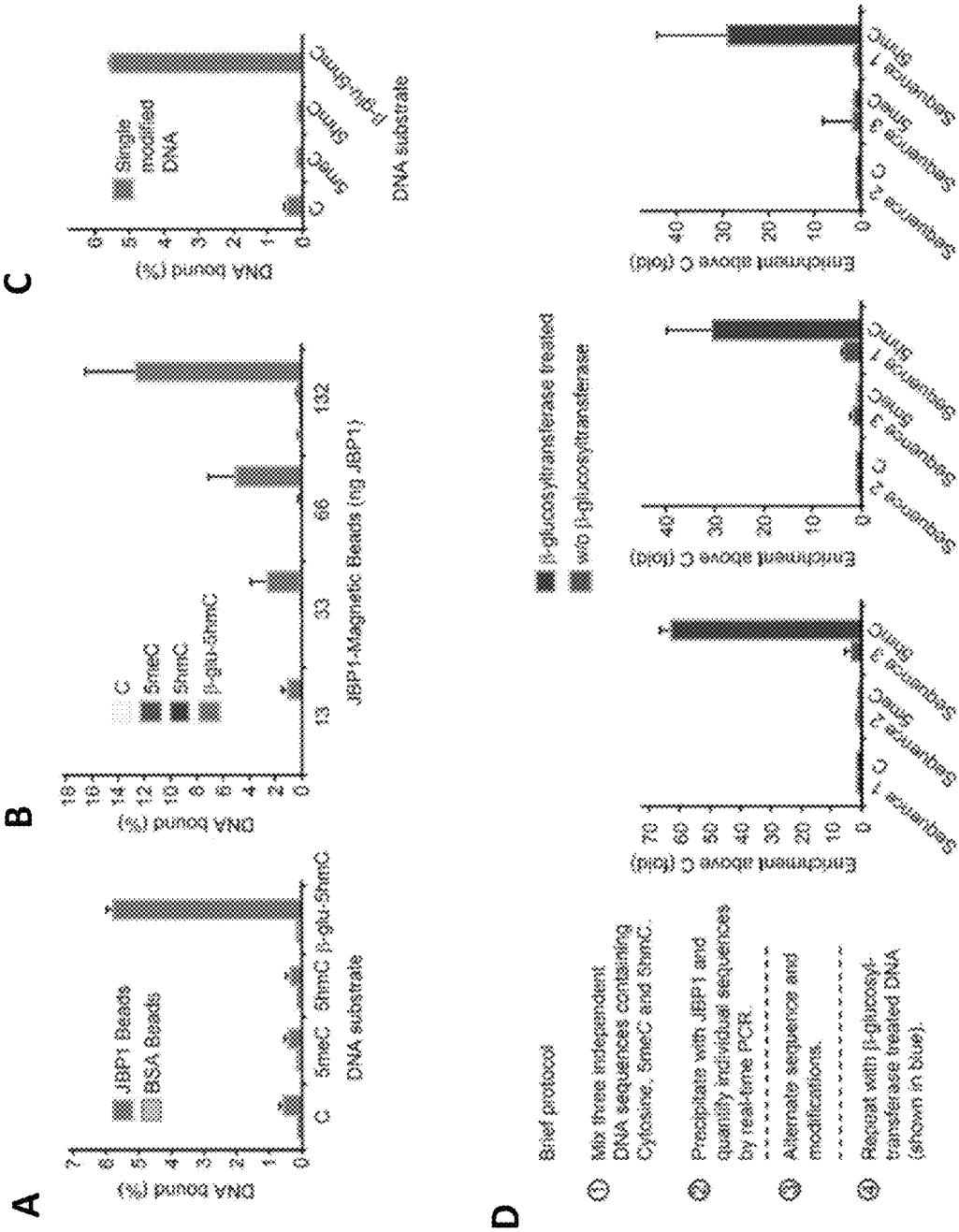
FIG. 5 shows that, in a sequence independent manner, JBP1 can selectively pull down DNA that contains β-glu-5hmC resulting from β-gt treatment. (a) Ten ng of each radiolabeled PCR product (Example 1) was incubated with magnetic beads coated with 132 ng JBP1 or 132 ng BSA. The beads were pulled down with a magnet and the percent bound to the beads was measured using scintillation counting. (b) 10 ng of each substrate were incubated in the same tube with various concentrations of JBP1 coated magnetic beads. The beads were pulled down using a magnet and the DNA that was bound to the magnetic beads was measured by quantitative real time PCR. (c) 208 fmol of 37 bp double stranded oligonuleotides containing unmodified cytosines, a single 5meC, 5hmC, or β-glu-5hmC on each strand were incubated with 132 ng JBP1 coated magnetic beads. Beads were pulled down as described and the percent DNA bound to the JBP1 coated magnetic beads was quantified using scintillation counting. (d) Three different combinations of three different PCR products composed of only cytosines, only 5meC, or 5hmC (20 ng of each) were combined and incubated with purified β-gt in the presence of UDP Glucose. The DNA was purified and incubated with 132 ng JBP1 coated magnetic beads. The JBP1 magnetic beads were pulled down as above and the amount of DNA pulled down was quantified using quantitative real time PCR. Data is presented as the fold enrichment over cytosine-containing DNA.

JBP1 coated magnetic beads (132 ng) could effectively pull down up to 6% of the DNA that contained the β-glu-5hmC modification (FIG. 5a). Additionally, JBP1 had little affinity for cytosine, 5meC, or 5hmC containing substrates. Furthermore, BSA coated magnetic beads were unable to pull down any of the substrates, suggesting that the binding of β-glu-5hmC is due to JBP1 bound to the magnetic beads.

The Efficiency of β-gly-5hmC Pull Down is Dependent on the Amount of JBP1 Coated Magnetic Beads Four different DNA substrates were created by PCR amplification of 4 different 2 kb mouse genomic regions (Sub1: contained only cytosines, Sub2 5me: contained 5meC at CpG dinucleotides, Sub3 5hmC: contained 5hmC instead of cytosines, Sub4 β-glu-5hmC: contained β-glu-5hmC instead of cytosines). These four substrates were incubated together with various concentrations of JBP1 coated magnetic beads. The beads were pulled down and the amount of each substrate captured was quantified using real time quantitative PCR. There was a clear dependence on the amount of JBP1 coated magnetic beads and the pull down efficiency (FIG. 5b). Furthermore it was demonstrated that the highest concentration of JBP1 coated magnetic beads could pull down 14% of the β-glu-5hmC DNA and provide an 87-fold enrichment of β-glu-5hmC modified DNA over cytosine containing DNA and a 319-fold enrichment over 5meC containing DNA.

JBP1 Can Pull Down DNA Containing a Single β-glu-5hmC Modification

The experiments described supra were conducted using substrates that contained many β-glu-5hmC modifications. It was desirable to determine whether a single β-glu-5hmC residue is sufficient for recognition by JBP1 coated magnetic beads. Therefore, four double stranded 37 bp substrates were created: the first containing unmodified cytosines, the second containing a single 5meC modification on each strand, the third contained a single 5hmC modification on each strand and the fourth contained a single β-glu-5hmC on each strand. Each of these substrates was $^{32}$P end-labelled and incubated with 132 ng JBP1 coated beads. After the substrate was incubated with JBP1 the bound fraction was measured by scintillation counting. JBP1 coated magnetic beads pull down the substrate containing a single β-glu-5hmC efficiently while showing little affinity for the other substrates composed of an identical sequence (FIG. 5c).

JBP1 Facilitated Pull Down of β-gt Treated 5hmC is Not Sequence Specific

An assay was performed that mimicked the JBP1 pull down used on mammalian DNA. Several different mixtures of DNA substrates were combined with differing sequences, with each substrate mixture containing unmodified cytosine substrate, 5meC modified substrate and 5hmC modified substrate. The substrate mixes were then treated with purified β-gt in the presence of UDP-glucose. The resulting DNA products were purified and incubated with JBP1 coated magnetic beads. In all three mixtures tested, the JBP1 coated magnetic beads were able to significantly enrich for the DNA substrate that contained the 5hmC modification after treatment with the β-gt (FIG. 5d). This result shows that JBP1 binding is not dependent on DNA sequence.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the medical sciences are intended to be within the scope of the following claims.

We claim:

1. An isolated biomolecule complex comprising a nucleic acid comprising a glucosylated 5-hydroxymethylcytosine base bound to a *C. fasciculata* J binding protein, wherein the *C. fasciculata* J binding protein is coated on a solid substrate.

2. The isolated biomolecule complex of claim 1, wherein said solid substrate is a bead.

3. The isolated biomolecule complex of claim 2, wherein said bead is selected from the group consisting of magnetic and polymer beads.

4. The isolated biomolecule complex of claim 1, wherein said *C. fasciculata* J binding protein is modified with a binding molecule.

5. The isolated biomolecule complex of claim 4, wherein said binding molecule is selected from the group consisting of biotin, avidin, a hapten, an immunoglobulin, and an aptamer.

* * * * *

SEQUENCE LISTING

```
<160> NUMBER OF SEQ ID NOS: 2

<210> SEQ ID NO 1
<211> LENGTH: 830
<212> TYPE: PRT
<213> ORGANISM: Crithidia fasciculata

<400> SEQUENCE: 1

Met Gly Ser Ser His His His His His His Ser Ser Gly Leu Val Pro
1               5                   10                  15

Arg Gly Ser His Met Glu Pro Lys Ser Lys Lys Val Lys Gln Asp Ile
            20                  25                  30

Phe Asn Phe Pro Asp Gly Lys Asp Val Pro Thr Thr Lys Glu Lys Ala
        35                  40                  45

Glu Ala Tyr Val Asp Ala Leu Lys Ala His Pro Phe Tyr Asp Asn Val
    50                  55                  60

His Ser Val Val Asp Val Tyr Asp Ser Ala Thr Leu Arg Asp Gly Lys
65                  70                  75                  80

Gly Arg Val Ile Gly Val Met Leu Arg Lys Ala Leu Pro Glu His Ala
                85                  90                  95

Thr Thr Ala Ala Gly Leu Leu Ser Ala Ala Ala Val Arg Thr Ser Leu
            100                 105                 110

Arg Ser Ser Met Phe Gly Gly Glu Ser Pro Leu Ser Gly Ile Ala Gly
        115                 120                 125
```

```
Tyr Phe Asp Tyr Arg Gly Ser Pro Val Glu Leu Lys Ala Arg Lys Thr
    130                 135                 140
Ala Phe Thr Tyr Glu His Glu Lys Lys Trp Pro Ala Val Phe Pro Leu
145                 150                 155                 160
Val Asp Tyr Val Ser Glu Ile Tyr Lys Ser Val Met Pro Glu His Trp
                165                 170                 175
Ala Ala Gln Asp Ser Ala Ile Pro Asp Ile Val Arg Ile His Gly Thr
            180                 185                 190
Pro Phe Ser Thr Leu Thr Ile Asn Ser Arg Phe Arg Thr Ala Ser His
        195                 200                 205
Thr Asp Ala Gly Asp Phe Asp Gly Gly Tyr Ser Cys Ile Ala Cys Ile
210                 215                 220
Asp Gly Asp Phe Lys Gly Leu Ala Leu Gly Phe Asp Asp Phe His Val
225                 230                 235                 240
Asn Val Pro Met Gln Pro Arg Asp Val Leu Val Phe Asp Ser His Tyr
                245                 250                 255
Phe His Ser Asn Ser Glu Leu Glu Ile Ser Cys Pro Thr Glu Glu Trp
            260                 265                 270
Arg Arg Leu Thr Cys Val Phe Tyr Tyr Arg Ser Ala Leu Gly Glu Pro
        275                 280                 285
Ser Ser Tyr Ala Glu Tyr Arg Arg Arg Leu Ala Ala Ala Gln Gln Asp
290                 295                 300
Ser Thr Ala Gln Pro Val Val Ser Ser Val Val Glu Lys Pro Asn Gly
305                 310                 315                 320
Lys Asn Leu Tyr Lys Pro Ser Thr Val Phe Pro Ile Asp Pro Thr Pro
                325                 330                 335
Phe Ala Val Val Ala Gln Leu His Arg Leu His His Cys Ala Ala Lys
            340                 345                 350
Gly Leu Cys Val His Glu Leu Ala Val Pro Ser Ser Pro Leu Ala
        355                 360                 365
Val Leu Leu Phe Gly Glu Arg Leu Ser Cys Ser Asp Gly Ile Pro Leu
370                 375                 380
Arg Ala Ala Glu Gln Lys Leu Lys Ala Asn Ala Asp Gly Ala Ser Arg
385                 390                 395                 400
Gly Val Thr Ser Ser Gly Gly Phe Ser Glu Ser Asp Ala Val Leu Thr
                405                 410                 415
Thr Ala Val Glu Lys Ser Lys Tyr Leu Glu Arg Asp His Leu Ser Gln
            420                 425                 430
Cys Ile Ser Ala Glu Leu Leu Ala Met Trp Val Glu Ala Arg Lys His
        435                 440                 445
Trp Leu Arg Leu Val Ala Thr Glu Trp Ala Arg Met Ile Ala Thr Ala
450                 455                 460
Pro Glu Arg Thr Asp Phe Leu Trp Lys Asn Lys Ser Pro Met Asn Thr
465                 470                 475                 480
Ala Phe Phe Asp Leu Cys Glu Val Ala Lys Gln Val Met Leu Gly Leu
                485                 490                 495
Leu Asp Lys Glu Thr Ala Thr Pro Thr Glu Glu Arg His Phe Trp Ser
            500                 505                 510
Val Tyr Ala Ala His Leu His Arg Ala Cys Ala Glu Arg Leu Met Met
        515                 520                 525
Pro Glu Glu Ala Met Ser Leu Arg Lys Leu Asn Val Lys Leu Lys Asp
530                 535                 540
```

```
Phe Ser Phe Gly Gly Thr Arg Tyr Phe Lys Asp Met Pro Val Glu Glu
545                 550                 555                 560

Gln Glu Arg Arg Val Ala Arg Lys Ala Ser Ile Glu Glu Ala Arg Arg
                565                 570                 575

Arg Ser Thr Ala Ala Lys Asp Gly Glu Gln Arg Ser Asn Trp Leu Thr
            580                 585                 590

Asn Asp Ala Phe Asp Tyr Gln Thr Glu Asp Cys Glu Val Asp Tyr Ala
            595                 600                 605

Gly His Gly Trp Ala Val Pro Lys Gln His Ala Lys Thr Val Thr Ala
        610                 615                 620

Asn Val His Gln Glu Ala Val Ala Ala Thr Thr Glu Ala Val Arg Val
625                 630                 635                 640

Leu Val Val Leu Pro Arg Pro Ser Gly Asp Arg Gly Asp Ala Ala
                645                 650                 655

Val Asp Leu Pro Lys Glu Val Thr Thr Ser Ala Glu Trp Val Arg Leu
                660                 665                 670

Met Ser Ser Pro Ala Val Arg Arg Val Leu Ala Ala Lys Gln Arg Asn
            675                 680                 685

Leu Thr Leu Leu Pro Asn Cys Asn Val Glu Ala Val Ser Leu Asn Phe
690                 695                 700

Ala Tyr His Asp Ser Leu Pro Gln Lys Ala Thr Phe Asp Phe Val Val
705                 710                 715                 720

Leu Gln His Val Leu Ser Ala Met Pro Glu Asp Ala Ile Ala Thr Asp
                725                 730                 735

Tyr Val Ser Arg Met Arg Ser Ile Cys Thr Gly Cys Leu Phe Val Val
                740                 745                 750

Glu Thr Asp Val Gln Cys Arg Gln Tyr Phe Thr Leu His Tyr Pro Leu
            755                 760                 765

Arg Val Gln Tyr Asp Ala Val Ala Pro Ala Phe Phe Gln Leu Leu His
            770                 775                 780

Arg Cys Ser Tyr Gly Thr Pro Leu Ala Arg Thr Arg Thr Lys Ala Glu
785                 790                 795                 800

Val Glu Ala Leu Phe Pro Phe Val Cys Cys Ala Arg Tyr Lys Leu Gln
                805                 810                 815

Gly Ser Pro Met Asn Thr Val Val His Leu Leu Ala Leu Glu
            820                 825                 830

<210> SEQ ID NO 2
<211> LENGTH: 371
<212> TYPE: PRT
<213> ORGANISM: T4 bacteriophage

<400> SEQUENCE: 2

Met Gly Ser Ser His His His His His His Ser Ser Gly Leu Val Pro
1               5                   10                  15

Arg Gly Ser His Met Lys Ile Ala Ile Asn Met Gly Asn Asn Val
            20                  25                  30

Ile Asn Phe Lys Thr Val Pro Ser Ser Glu Thr Ile Tyr Leu Phe Lys
        35                  40                  45

Val Ile Ser Glu Met Gly Leu Asn Val Asp Ile Ser Leu Lys Asn
    50                  55                  60

Gly Val Tyr Thr Lys Ser Phe Asp Glu Val Asp Val Asn Asp Tyr Asp
65                  70                  75                  80

Arg Leu Ile Val Val Asn Ser Ser Ile Asn Phe Phe Gly Gly Lys Pro
                85                  90                  95
```

```
Asn Leu Ala Ile Leu Ser Ala Gln Lys Phe Met Ala Lys Tyr Lys Ser
            100                 105                 110

Lys Ile Tyr Tyr Leu Phe Thr Asp Ile Arg Leu Pro Phe Ser Gln Ser
            115                 120                 125

Trp Pro Asn Val Lys Asn Arg Pro Trp Ala Tyr Leu Tyr Thr Glu Glu
    130                 135                 140

Glu Leu Leu Ile Lys Ser Pro Ile Lys Val Ile Ser Gln Gly Ile Asn
145                 150                 155                 160

Leu Asp Ile Ala Lys Ala Ala His Lys Lys Val Asp Asn Val Ile Glu
                165                 170                 175

Phe Glu Tyr Phe Pro Ile Glu Gln Tyr Lys Ile His Met Asn Asp Phe
            180                 185                 190

Gln Leu Ser Lys Pro Thr Lys Lys Thr Leu Asp Val Ile Tyr Gly Gly
            195                 200                 205

Ser Phe Arg Ser Gly Gln Arg Glu Ser Lys Met Val Glu Phe Leu Phe
    210                 215                 220

Asp Thr Gly Leu Asn Ile Glu Phe Phe Gly Asn Ala Arg Glu Lys Gln
225                 230                 235                 240

Phe Lys Asn Pro Lys Tyr Pro Trp Thr Lys Ala Pro Val Phe Thr Gly
                245                 250                 255

Lys Ile Pro Met Asn Met Val Ser Glu Lys Asn Ser Gln Ala Ile Ala
            260                 265                 270

Ala Leu Ile Ile Gly Asp Lys Asn Tyr Asn Asp Asn Phe Ile Thr Leu
            275                 280                 285

Arg Val Trp Glu Thr Met Ala Ser Asp Ala Val Met Leu Ile Asp Glu
            290                 295                 300

Glu Phe Asp Thr Lys His Arg Ile Ile Asn Asp Ala Arg Phe Tyr Val
305                 310                 315                 320

Asn Asn Arg Ala Glu Leu Ile Asp Arg Val Asn Glu Leu Lys His Ser
                325                 330                 335

Asp Val Leu Arg Lys Glu Met Leu Ser Ile Gln His Asp Ile Leu Asn
            340                 345                 350

Lys Thr Arg Ala Lys Lys Ala Glu Trp Gln Asp Ala Phe Lys Lys Ala
            355                 360                 365

Ile Asp Leu
    370
```